United States Patent [19]

Hubbs et al.

[11] Patent Number: 5,214,145
[45] Date of Patent: May 25, 1993

[54] TRISUBSTITUTED PIPERAZIN-2,5-DIONES

[75] Inventors: John C. Hubbs; Charles H. Foster, both of Kingsport, Tenn.

[73] Assignee: Eastman Kodak Company, Rochester, N.Y.

[21] Appl. No.: 647,618

[22] Filed: Jan. 28, 1991

Related U.S. Application Data

[60] Division of Ser. No. 406,995, Sep. 14, 1989, Pat. No. 4,992,552, which is a continuation-in-part of Ser. No. 239,492, Aug. 31, 1988, abandoned.

[51] Int. Cl.$^5$ ............................................. C07D 241/08
[52] U.S. Cl. ...................................... 544/385; 560/19; 562/443
[58] Field of Search .......................................... 544/385

[56] References Cited

U.S. PATENT DOCUMENTS

| | | | |
|---|---|---|---|
| 4,293,648 | 10/1981 | Davino | 435/70 |
| 4,634,790 | 1/1987 | Shinohara et al. | 560/40 |
| 4,668,625 | 5/1987 | Cambiaghi et al. | 435/70 |
| 4,677,220 | 6/1987 | Tou et al. | 560/40 |

Primary Examiner—C. Warren Ivy
Assistant Examiner—James H. Turnipseed
Attorney, Agent, or Firm—Mark A. Montgomery; William P. Heath, Jr.; T. R. Savitsky

[57] ABSTRACT

Disclosed is a process for preparation of an amino acid, such as phenylalanine, with a high degree of optical purity. The process makes use of the same amino acid as a chiral template.

9 Claims, No Drawings

TRISUBSTITUTED PIPERAZIN-2,5-DIONES

This is a divisional of copending application Ser. No. 07/406,995 filed on Sep. 14, 1989, now U.S. Pat. No. 4,992,552 which is a continuation-in-part of Ser. No. 07/239,492, filed Aug. 31, 1988 now abandoned.

FIELD OF INVENTION

The present invention concerns a process for synthesis of an amino acid wherein the same amino acid serves as its own chiral template.

BACKGROUND OF THE INVENTION

Amino acids are the building blocks of proteins and are therefore essential for life itself. Amino acids can be either of the type found in proteins of biological sources (so called naturally occurring) or can be of other types that are synthesized chemically (so called synthetic amino acids). Amino acids of either the naturally occurring type or the synthetic type have a multitude of uses including use as a nutritional source or intermediate therefor and use as building blocks for various biologically active peptides and proteins (e.g. see for example, C. Y. Bowers, et. al., European Patent Application WO 87/06835).

Alpha-amino acids typically have one asymmetric carbon atom and therefore can be either in the L or D form. In most cases the L form is the form found in proteins of biological sources. For various applications it is desirable to have only one optically active form of the amino acid (rather than the other form or a racemic mixture). Therefore processes for production of an amino acid with a particular degree of optical purity are highly desirable.

SUMMARY OF THE INVENTION

The present invention is directed to a process for preparation of a substantially optically pure alpha-amino acid wherein the same amino acid serves as its own chiral template. The process of the present invention employs a novel hydrogenation step wherein a cyclic compound having an asymmetric carbon of either L or D configuration and an unsaturated carbon-carbon double bond is converted to a cyclic compound with two asymmetric carbon atoms in substantially the cis-form. Such hydrogenation step shall be referred to herein as "the hydrogenation step". More specifically, the hydrogenation step comprises Contacting Compound I of the formula

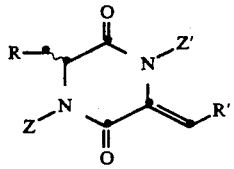

(I)

wherein R is hydrogen, hydroxy, alkyl, aryl, $C_1$ to $C_{10}$ substituted alkyl, $C_1$ to $C_{10}$ alkoxy, $C_7$ to $C_{12}$ arylalkyl, $C_7$ to $C_{12}$ substituted arylalkyl, $C_1$ to $C_{10}$ carboxyalkyl or $C_1$ to $C_{10}$ acyloxy, R' is the same as R; Z is a nitrogen-protecting group or hydrogen; and Z' is the same or different than Z and is a nitrogen-protecting group or hydrogen; with hydrogen in the presence of a suitable catalyst and suitable solvent to form compound II of the formula

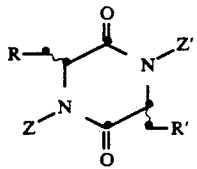

(II)

wherein the diastereomeric purity of compound II is at least about 70%, preferably at least about 90% of the cis derivative, more preferably at least about 95% of the cis derivative.

As used herein, diastereomeric purity refers to the % cis isomer and can be expressed mathematically as % diastereomeric purity $$dp = \left| \frac{\text{amt. of cis isomer}}{\text{amt. of cis isomer + amount of trans isomer}} \right| \times 100$$

DETAILED DESCRIPTION OF THE INVENTION

The undulating lines (i.e. ∼) connecting various substituents in the formulas appearing herein indicate bonds wherein the stereochemistry of the asymmetric carbon atom containing the bond (∼) is independently in the D or L configuration. As used herein "D" or "L" configuration refers to the chirality of the carbon atom adjacent to the carbonyl carbon (the alpha position); such carbon atom is hereinafter referred to as the alpha carbon atom in amino acids and amino acid derivatives. The terms D-configuration and L-configuration are commonly understood to those experienced in the art (e.g., see, pp. 80–83, A. L. Lehninger, *Biochemistry, Second Edition*, Worth Publishers, Inc., New York, New York, 1977).

It is to be understood that when one or more steps are performed consecutively wherein a compound has two asymmetric alpha carbon atoms as indicated, such two asymmetric carbon atoms will be substantially in the cis form. As used in this context "substantially" means that at least about 70%, more preferably at least about 90% and most preferably at least about 95% of the desired compound will be in the desired form.

As used herein the term "optical purity" refers to an amino acid or derivative thereof and can be expressed mathematically in percent as an absolute value as $$op = \left| \frac{\% \text{ L isomer} - \% \text{ D isomer}}{\% \text{ L isomer} + \% \text{ D isomer}} \right| \times 100$$

The term "alkyl" means straight, branched or cyclic alkyl moieties of up to 20 carbon atoms such as methyl, ethyl, n-propyl, isopropyl, n-butyl, sec-butyl, pentyl, hexyl, heptyl, octyl, nonyl, decyl, and dodecyl. Preferred alkyl groups are $C_1$ to $C_{10}$, more preferred are $C_1$ to $C_6$, and most preferred are methyl, isopropyl, and isobutyl.

The term "$C_1$ to $C_{10}$ substituted alkyl" denotes the above $C_1$ to $C_{10}$ alkyl groups that are substituted by one to four halogen, hydroxy, amino, $C_1$ to $C_7$ acyloxy, nitro, carboxyalkyl, carbamoyloxy, cyano, or $C_1$ to $C_6$ alkoxy groups. The substituted alkyl groups may be substituted once or up to four times with the same or with different substituents. Preferred substituted alkyl are $C_1$ to $C_6$ substituted alkyl groups.

Examples of the above substituted alkyl groups include the cyanomethyl, nitromethyl, hydroxymethyl, trityloxymethyl, propionyloxymethyl, aminomethyl, carboxymethyl (i.e., $-CH_2-COOH$), allyloxycarbonylmethyl, allyloxycarbonylaminomethyl, carbamoyloxymethyl, methoxymethyl, ethoxymethyl, 1-butoxymethyl, acetoxymethyl, chloromethyl, bromomethyl, iodomethyl, 6-hydroxyhexyl, 2-amino(iso-propyl), 2-carbamoyloxyethyl and the like. A preferred group of examples within the above "$C_1$ to $C_{10}$ substituted alkyl" group includes the substituted methyl group, in other words, a methyl group substituted by the same substituents as the "$C_1$ to $C_{10}$ substituted alkyl" group. Examples of the substituted methyl group include groups such as hydroxymethyl, acetoxymethyl, carbamoyloxymethyl, carboxymethyl, chloromethyl, bromomethyl and iodomethyl.

The term "$C_1$ to $C_{10}$ alkoxy" as used herein denotes groups of the formula $OR^7$ wherein $R^7$ is hydrogen or alkyl. Preferred alkoxy groups include such groups as methoxy, ethoxy, n-propoxy, isopropoxy, butoxy, and like groups.

The term "$C_1$ to $C_{10}$ acyl" or "acyl" denotes groups of the formula

containing between 1 and 10 carbon atoms, wherein $R^3$ is hydrogen, alkyl, aryl, substituted alkyl, arylalkyl, and substituted arylalkyl. Examples of preferred $C_1$ to $C_{10}$ acyl groups are those wherein $R^3$ is a $C_1$ to $C_6$ alkyl group such as methyl (Me), ethyl (Et), propyl (Pr) or butyl (bu).

The term "enol ester" refers to a compound of the formula

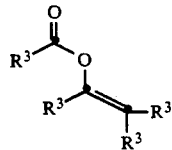

wherein $R^3$ is defined hereabove.

The term "$C_1$ to $C_{10}$ acyloxy" or "acyloxy" denotes groups of the formula

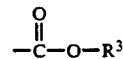

containing between 1 and 10 carbon atoms, wherein $R^3$ is as defined hereabove. Examples of preferred $C_1$ to $C_{10}$ acyloxy groups include those wherein $R^3$ is a $C_1$ to $C_6$ alkyl group such as methyl, ethyl, propyl, or butyl. Additional preferred acyloxy groups include those wherein $R^3$ is aryl or arylalkyl such as phenyl or benzyl.

The term "$C_1$ to $C_{10}$ carboxylalkyl" denotes groups of the formula

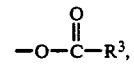

wherein $R^3$ is as defined hereabove. Examples of preferred $C_1$ to $C_{10}$ carboxyalkyl groups are those wherein $R^3$ is a $C_1$ to $C_6$ alkyl group such as methyl, ethyl, propyl or butyl.

The term "aryl" refers to aromatic groups of 3 to 50 carbon atoms which include heterocyclic rings and unsubstituted and substituted aryls. The most preferred aryl is phenyl.

The term "substituted aryl" specifies an aryl group (preferred is a phenyl group) substituted with one to four moieties chosen from the group consisting of halogen, hydroxy, protected hydroxy, cyano, nitro, $C_1$ to $C_4$ alkyl, $C_1$ to $C_4$ alkoxy, carboxy, carboxymethyl, hydroxymethyl, aminomethyl, trifluoromethyl or N-(methylsulfonylamino). Phenyl shall be alternately referred to herein by the symbols "φ" or "Ph".

Examples of the term "substituted aryl" include mono-, di- or tri(halo) phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, and the like; a mono-, di , or tri(hydroxy)phenyl group such as 4-hydroxyphenyl, 3-hydroxyphenyl, 2,4-dihydroxyphenyl, the protected hydroxy derivative thereof, and the like, a nitrophenyl group such as 3 or 4-nitrophenyl, a mono-, di- or tri(-lower alkyl)phenyl group such as 4-methylphenyl, 2,4-dimethylphenyl, 2-methylphenyl, 4-(iso-propyl)phenyl, 4-ethylphenyl, 3-(n-propyl)phenyl, and the like; a mono- di or tri(alkoxy)phenyl group, for example 2,6-dimethoxyphenyl, 4-methoxyphenyl, 3-ethoxyphenyl, 3-(isopropoxy)phenyl, 4-(t-butoxy)phenyl, 3,4,5-trimethylphenyl, 3-ethoxy-4-methoxyphenyl, and the like; a mono- or dicarboxyphenyl group such as 4-carboxyphenyl; a mono- or di(hydroxymethyl)phenyl such as 3,4-di(hydroxymethyl)phenyl; a mono- or di(aminomethyl)phenyl such as 2-(aminomethyl)phenyl or a mono- or di (N-(methysulfonylamino))phenyl such as 3-(N-(methylsulfonylamino))phenyl. Also, the term "substituted phenyl" represents disubstituted or trisubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like.

The terms "halo" and "halogen" refer to the fluoro, chloro, bromo or iodo groups.

The term $C_7$ to $C_{12}$ arylalkyl denotes a $C_1$ to $C_6$ alkyl group substituted at any position by a aromatic ring. Examples of such a group include phenylmethyl (benzyl), 2-phenylethyl, 3-phenyl(n-propyl), 4-phenylhexyl, 3-phenyl-(n-amyl), 3-phenyl-(sec-butyl), and the like. A preferred group is the benzyl group.

The term "$C_7$ to $C_{12}$ substituted arylalkyl" denotes a $C_7$ to $C_{12}$ arylalkyl group substituted on the $C_1$ to $C_4$ alkyl portion with one or two groups chosen from halogen, hydroxy, $C_1$ to $C_7$ acyloxy, nitro carboxy, carbamoyl, carbamoyloxy, cyano, N-(methylsulfonylamino) or $C_1$ to $C_4$ alkoxy; and/or the aromatic group may be substituted with 1 or 2 groups chosen from halogen, hydroxy, nitro, $C_1$ to $C_4$ alkyl, $C_1$ to $C_4$ alkoxy, carboxy, carboxymethyl, hydroxymethyl, aminomethyl, or a N-(methylsulfonylamino) group. As before, when either the $C_1$ to $C_4$ alkyl portion or the aromatic portion or both are disubstituted, the substituents can be the same or different.

Examples of the term "$C_7$ to $C_{12}$ substituted arylalkyl" include groups such as 2-phenyl-1-chloroethyl, 2-(4-methoxyphenyl)ethyl, 2,6-dihydroxy-4-phenyl(n-hexyl), 5-cyano-3-methoxy-2-phenyl(n-pentyl), 3-(2,6-dimethylphenyl)n-propyl, 4-chloro-3-aminobenzyl, 6-(4-methoxyphenyl) -3-carboxy(n-hexyl), 5-(4-aminomethyl-phenyl) 3-(amino)-(n-hexyl), and the like.

The term "heterocyclic ring" denotes optionally substituted five-membered or six-membered rings that have 1 to 4 heteroatoms, such as oxygen, sulfur and/or nitrogen, in particular nitrogen, either alone or in conjunction with sulfur or oxygen ring atoms. These five-membered or six-membered rings may be fully unsaturated or partially unsaturated with fully unsaturated rings being preferred.

Furthermore, the above optionally substituted five-membered or six-membered rings can optionally be fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heterocyclic ring" and are non-limiting: thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiaziayl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, oxhydropyrimidyl, tetrahydropyrimidyl, tetrazolo(1,5-b)pyridaziny; and purinyl, as well as benzo-fused derivatives for example benzoxazolyl, benzthiazolyl, benzimidazoly and indolyl.

A preferred group of examples of the above heterocyclic rings are 5-membered ring systems containing a sulfur or oxygen atom and/or one to three nitrogen atoms. Examples of such preferred groups include thiazolyl, thiadiazolyl, and oxazolyl. A group of further preferred examples of 5-membered ring systems with 2 to 4 nitrogen atoms include imidazolyl, triazolyl, and tetrazolyl.

Further specific examples of the above heterocyclic ring systems are 6-membered ring systems containing one to three nitrogen atoms. Such examples include pyridyl, pyrimidyl, triazinyl, pyridazinyl, and pyrazinyl.

The substituents for the optionally substituted heterocyclic ring systems and further examples of the 5- and 6-membered ring systems discussed above, are found in W. Durckheimer et at., U.S. Pat. No. 4,278,793, incorporated herein by reference issued Jul. 14, 1981, columns 9 through 21 and columns 33 through 188 (examples of the term "heterocyclic ring" are included in the heterocyclic thiomethyl groups listed under heading "A").

The more preferred aryls are phenyl, naphthyl, pyridyl, and indole; and the most preferred aryl is phenyl.

The term "nitrogen-protecting group" as used in the specification and claims refers to substituents of an amide or amino group commonly employed to block or protect the amino or amide functionality while reacting other functional groups on the compound. Examples of such nitrogen-protecting groups include but are not limited to acetyl, the formyl group, the trityl group, the phthalimido group, the trichloracetyl group, the chloroacetyl, bromoacetyl, and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenxyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 1,1-diphenyleth-1-yloxycarbonyl, 1,1-diphenylprop-1-yloxcarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)-ethoxycarbonyl, 2-(triphenylphosphino)-ethoxycarbonyl, 9-fluorenylmethoxycarbonyl ("FMOC"), t-butoxycarbonyl ("BOC"), 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group and like amino-protecting groups. The species of nitrogen-protecting group employed is not critical so long as the derivatized amide or amino group is stable to the conditions of subsequent reaction(s) which effect other positions of the molecule and can be removed at the appropriate point without disrupting the important functional group(s) of the subsequent product molecule(s). Preferred nitrogen-protecting groups are the allyloxycarbonyl, the benzyloxycarbonyl, t-butoxycarbonyl, trityl, acetyl and substituted acetyl groups. The most preferred nitrogen protecting groups are acetyl (Ac) and alpha-halo-acetyl. Similar amino-protecting groups used in the peptide art are also embraced by the above term. Further examples of groups referred to by the above term are described by J. W. Barton, "Protective Groups in Organic Chemistry", J. G. W. McOmie, Ed., Plenum Press New York, N.Y., 1978 Chapter 2, and T. W. Greene, "Protective Groups in Organic Synthesis", John Wiley and Sons, New York, N.Y. 1981, Chapter 7. The related term "Protected nitrogen" defines an amino or amide group substituted with a nitrogen-protecting group discussed above.

A preferred process for the present invention involves several steps starting with one mole of a substantially optically pure amino acid and ending with approximately two moles of the same amino acid having the same optical configuration and substantially the same optical purity. The preferred amino acids for use in the present invention include phenylalanine, isoleucine, leucine, lysine, methionine, threonine, tryptophan, valine, alanine, aspartic acid, glutamic acid, arginine, asparagine, cysteine, glutamine, histidine, serine, and tyrosine.

The most preferred amino acid is phenylalanine, especially L-phenylalanine.

In the preferred compounds described herein R and R' are the same and are preferably aryl with phenyl and substituted phenyl being more preferred, and phenyl being most preferred; generally for Compounds I and II, Z' is preferably H. For Compounds I and II, Z is preferably acyl, acyloxy, or hydrogen. For compounds I and II, Z is most preferably acetyl or hydrogen.

Regarding the Q substituents of the compounds described hereinafter, Q is capable of being displaced by a nitrogen-containing nucleophile, preferably ammonia or a substituted mine. Many Q groups are often referred to in the art as esters or active esters, and are commonly used as activating groups in the peptide art. Example of Q groups are described by M. Bodansky in "Active Esters in Peptide Synthesis," pp. 105-196, The Peptides, I, E. Gross, J. Meienhofer, editors, Academic Press, New York, New York, 1979. Except for compounds ZQ and $Z^1Q$ described hereinafter, preferred Q groups include chloro, bromo, iodo, —$SR^4$ or $OR^4$ wherein $R^4$ is H, alkyl, aryl, $C_1$ to $C_{10}$ substituted alkyl, $C_7$ to $C_{12}$ arylalkyl, $C_7$ to $C_{12}$ substituted arylalkyl, $C_1$ to $C_{10}$ acyl, and $C_1$ to $C_{10}$ acyloxy. Other Q substituents are nitrogen-containing cyclic moieties such as imidazole, succinimide, and phthalimide.

The first step ("Step 1") of the process of the present invention is a process for preparing a compound of the formula

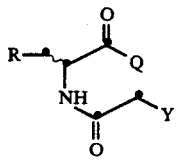
(III)

which comprises contacting a compound of the formula

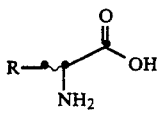
(IV)

or salt form thereof with either
(a) a compound of the formula

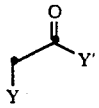
(V)

in the presence of a suitable solvent and under acidic, neutral, or basic conditions and under other conditions such that a compound is formed having the following formula

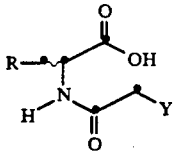
(VI)

followed by reacting Compound VI with a suitable nucleophile of the formula

HQ (VII)

in the presence of a suitable solvent under conditions such that an actual or formal loss of water occurs and Compound III is formed, or
(b) a suitable nucleophile of the formula

HQ (VII)

in the presence of a suitable solvent, under conditions such that there is formed a compound of the formula

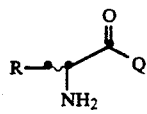
(VIII)

or salt form thereof followed by reacting compound VIII with compound V in a suitable solvent under conditions such that compound III is formed;

wherein Q is as defined hereinbefore; and Y is a group capable of undergoing nucleophilic displacement most preferably with ammonia to introduce nitrogen at the carbon atom substituted with Y, or is amino or an amino group substituted with one or two nitrogen-protecting groups, and Y' is a group capable of undergoing nucleophilic displacement. Y' groups are capable of undergoing nucleophilic displacement upon reaction with compound IV or compound VIII. Examples of such groups include halo and alcohol leaving groups known in the art such as tosylates and mesylates. In the case where Y is amino or an amino group substituted with one or two nitrogen protecting groups, while Y may in some cases be capable of undergoing nucleophilic displacement, such a displacement is not generally necessary to introduce nitrogen at the carbon atom substituted with Y.

Suitable solvents for Step 1 as well as for the steps that follow are those solvents capable of solubilizing the reactants sufficiently enough to allow the desired process step to proceed without significant adverse effects. Suitable solvents for Step 1 include polar or nonpolar, protic or aprotic solvents such as $C_1$ to $C_{10}$ aliphatic or aromatic alcohols, e.g., methanol (MeOH), ethanol (EtOH) and isopropanol (iPrOH); dimethylformamide; tetrahydrofuran; water; $C_1$-$C_{20}$ straight chain or branched chain carboxylic acids or esters derived therefrom; toluene; methylene chloride; and mixtures thereof. As appreciated in the art, varying solvents and other process conditions may affect the process steps. Routine experimentation may be required to determine desired or optimal process conditions.

Preferred conditions for Step (1)(a) include reacting compound IV with compound V under basic conditions and a reaction temperature of about $-80°$ to $300°$ C., more preferred is $-20°$ to $100°$ C.; and most preferred is about $0°$ to $40°$ C. Preferred molar ratios of compound IV:compound V are about 1:10 to 10:1; preferred is 1:3 to 3:1.

Preferred conditions for Step (1)(a) involve reacting compound VI with compound VII to produce Compound III, and include use of a $C_1$ to $C_{10}$ aliphatic or aromatic alcohol, more preferably the solvent is the same as the nucleophile (i.e., compound VII). The most preferred solvents are MeOH, EtOH, iPrOH, and benzyl alcohol. This reaction is also preferably performed under acidic conditions and/or in the presence of a dehydrating agent in the amount necessary to dehydrate the carboxylic acid moiety of compound VI. Such dehydrating agents include 4A molecular sieves, 3A molecular sieves, magnesium sulfate, dicyclohexylcarbodiimide and related carbodiimides, carbonyldiimidazole, thionyl chloride, and the like. The preferred reaction temperatures for reacting compound VI with compound VII are about the same as those for reacting compound IV with compound V, except that in the former case, in acidic conditions with alcohol solvents, higher temperatures are generally preferred. Molar ratios of compound VI:compound VII are preferably 1:1000 to 10:1; 1:1 to 1:100 being more preferred.

Other preferred conditions for step 1(a) include reacting a compound of the formula IV with an alpha-haloacetyl halide (V) wherein Y and Y' are chosen from the group consisting of chlorine, bromine, and iodine to produce a compound of the formula VI. Alternatively, IV may be allowed to react with glycine or an appropriately protected and/or activated form of glycine such that a glycine substituted dipeptide VI is formed wherein Y is either $NH_2$ or an appropriately substituted nitrogen atom.

Other preferred conditions for the conversion of VI to III include reacting a compound of the formula VI wherein Y is defined as above with a $C_1$ to $C_{10}$ aliphatic alcohol under conditions which permit dehydration to form an ester linkage.

Preferred conditions for Step(1)(b) include the same preferred molar ratios of reactants as described for Step (1)(a). Also, the preferred reaction temperatures for Step (1)(b) are about the same as for Step (1)(a). Step (1)(b) also proceeds with an actual or formal loss of water.

Other preferred conditions for step 1(b) include reacting a compound to the formula IV with a $C_1$ to $C_{10}$ aliphatic alcohol to produce VIII under conditions which permit actual or formal dehydration to form an ester linkage.

Other preferred conditions for the conversion of VIII to III include reacting a compound of the formula VIII (wherein $Q=OR^4$ and $R^4$ is a $C_1$ to $C_{10}$ straight or branched chain alkyl or aryl group) with a compound of the formula V wherein Y and Y' are chosen from the group consisting of chlorine, bromine, and iodine to produce a compound of the formula III. Optionally, halogen exchange (preferably with iodine) may be effected on a compound of formula III to produce a more reactive compound Also, Compound VIII may be allowed to react with glycine or an appropriately protected and/or activated form of glycine such that a glycine substituted dipeptide III is formed wherein Y is either $NH_2$ or an appropriately substituted nitrogen atom.

The second step ("step 2") of the present invention comprises contacting compound III with a compound of the formula $$HNWW'$$ (IX)

wherein W and W' are nitrogen-protecting groups or hydrogen. W may be the same or different than W'. It is most preferred that W and W' be hydrogen. Step 2 is permitted to occur in the presence of an appropriate solvent, under conditions such that a compound is formed having the following formula

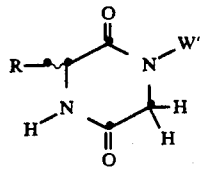

(X)

In the case where in Compound III Y is amino or an amino group substituted with one or two nitrogen protecting groups, III can be directly converted to X without the need to contact III with IX. In some cases it may be necessary to remove protecting groups (W and/or W') from III to form X when Y is an amino group substituted with one or two nitrogen protecting groups.

It is to be understood that various intermediates resulting from reaction of IX with III may be isolated (for example III where $Y=NH_2$). These intermediates can then in turn be converted to X.

Appropriate solvents for Step 2 are the same as described for Step (1). A preferred reaction temperature for Step 2 is about −80° to 300° C. with −20° to 40° C. being more preferred. Preferred molar ratios of compound IX:compound III are about 10,000:1 to 1:1 with about 1,000:1 to 1:1 being more preferred.

Other preferred conditions for Step 2 include reacting a compound of the formula III where $Q=OR^4$ where $R^4$ is defined as described hereinbefore and Y=-halogen with ammonia in a $C_1$ to $C_{10}$ alcohol solvent such as methanol, ethanol, phenol, benzyl alcohol, n-propanol, etc. Certain reactants, e.g., ammonia, can be used as solvent.

Alternatively, the cyclic dipeptide X may be prepared from an ester of a linear dipeptide containing an appropriate N-terminal amino acid and a C-terminal glycine which is itself prepared by condensation of an N-protected amino acid and an unprotected or carboxy-protected glycine.

The third step ("Step 3") of the present invention comprises reacting compound X with compounds of the formula ZQ, and Z'Q wherein QH and/or QW' are actually or formally liberated in the reaction, in the presence of an appropriate solvent and, optionally, at least a catalytic amount of a suitable catalyst, under conditions such that a compound is formed having the formula

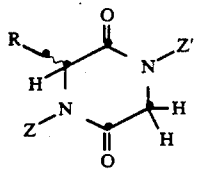

(XI)

wherein Z, Z', R, and Q are defined hereabove. However, in formula XI it is preferred that Z and Z' be the same and not hydrogen. It is even more preferred that Z and Z' both be acyl or acyloxy. More preferred is acyl, and most preferred is acetyl.

Appropriate solvents for Step 3 are the same as described for Step 1 and additionally include an acyl anhydride such as alkyl

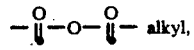

preferably wherein the alkyl groups contain 1 to 6 carbon atoms; preferred solvents are $C_1$ to $C_{20}$ straight chain or branched chain carboxylic acids, and aprotic solvents such as ethyl acetate, THF, DMF, toluene, or the like. It is preferred that compounds ZQ and Z'Q are the same. The nature of the Q group in ZQ and/or Z'Q is generally not important so long as the Q group permits the incorporation of Z and Z' in the conversion of X to XI. Preferred compounds that can be ZQ and/or Z'Q include acyloxy halides such as benzyl chloroformate, acyl anhydrides such as acetic anhydride or enol esters or enol acyloxy compounds such as isopropenyl acetate. It is also preferred that ZQ and/or Z'Q act as the reaction's suitable solvent. A large molar excess of ZQ and Z'Q to Compound X is therefore possible, but usually at least about 1 mole equivalent of each of ZQ and Z'Q are desired.

Preferred reaction temperatures for Step 3 are about $-20°$ to $300°$ C. with about $50°$ to $150°$ C. being more preferred.

Preferred catalysts for Step 3 are acid catalysts, e.g., strong acid or weak acid catalysts. Such catalysts include $Cu^{II}Cl_2$ p-toluene sulfonic acid (TsOH), and acetic acid. Preferred catalytic amounts (or more) include a molar ratio of catalyst:Compound X of about 1:100,000 to 10:1; especially preferred for weak acid catalyst is about 1:1,000 to 10:1 with about 1:20 to 10:1 being more preferred; especially preferred for strong acid catalysts is about 1:2000 to 1:100.

In a preferred embodiment of the invention, Z and Z' impart the property of crystallinity such that upon crystallization from a suitable solvent, Compound XI can be obtained in wholly or substantially optically pure form. For this crystallization step, a suitable solvent is ethyl acetate-heptane mixture. Preferred optical purity after crystallizing Compound XI is greater than about 90%, more preferably greater than about 95%, and most preferred is greater than about 99%. For this crystallization it is preferred that Z' and Z are the same and are acyl or acyloxy, more preferred Z and Z' are acetyl or alpha-halo-acetyl. The physical steps for crystallization simply include contacting Compound XI with solvent such that the desired compound crystallizes, i.e., forms a crystalline solid. The desired compound can then be separated or isolated by conventional techniques such as filtration.

In the case where $W'=Z=Z'=H$, step 3 is not necessary and in further steps Compound X and XI are the same.

The fourth step ("step 4") of the present invention comprises contacting Compound XI with either a. A compound of the formula $$R'-CHO \quad\quad\quad (XII)$$

or b. a compound of the formula

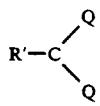
(XIII)

wherein each Q and R', independently, are as defined hereabove, in the presence of an acid or base and a suitable solvent, under conditions such that a compound is formed having the formula

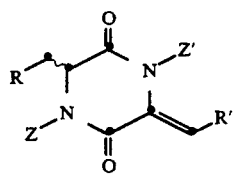
(I)

wherein R, R', Z, and Z' are as defined hereabove and R is the same as R'. Suitable solvents for Step 4 are the same as described for Step 1.

Preferred conditions for Step 4(a) include reaction of XI with a strong base such as potassium t-butoxide (KOtbu), in an aprotic solvent, or in a $C_1$ to $C_{10}$ aryl or alkyl or alkylaryl alcohol and permitting reaction of the deprotonated intermediate derived from Compound XI with Compound XII.

Preferred conditions for Step 4(b) include permitting a deprotonated intermediate formed as described above to react with compound XIII.

Preferred reaction temperatures for Step 4 are about $-80°$ to $100°$ C.; more preferred is $-20°$ to $100°$ C.; most preferred is about $-20°$ to $25°$ C. Preferred molar ratios of Compound XI to Compound XII or Compound XIII are about 1:10 to 1:1.

The fifth step ("step 5") of the present invention is the novel hydrogenation step described in the "Summary of the Invention" section.

Suitable solvents for Step 5 are the same as described for Step 1. Preferred solvents for step 5 include acetic acid, DMF, and $C_1$ to $C_{10}$ alcohols, such as MeOH, EtOH, and iPrOH. Preferred reaction temperatures for Step 5 are about $-80°$ to $100°$ C.; more preferred is about $-80°$ to $50°$ C.; most preferred is about $-50°$ to $25°$ C. Lower temperatures are generally preferred to enhance diastereomeric selectivity in reduction. In Step 5, hydrogen can be hydrogen gas or other source of hydrogen.

Suitable catalysts for Step 5 are common hydrogenation catalysts known in the art such as transition metal catalysts. Examples include palladium on carbon (Pd-C), palladium on aluminum, and the like. Molar ratio of hydrogen to Compound I are not known to be critical but typically an excess of hydrogen is used. The amount of catalyst is a catalytic amount or greater; typically a molar ratio of catalyst:Compound I of about 1:100,000 to 10:1 is used. A preferred molar ratio of catalyst:Compound I is about 1:10,000 to 1:1,000.

It is contemplated that when Z and/or Z' are not H, one can optionally treat I or II to convert Z and/or Z' into H.

The sixth step ("step 6") of the present invention comprises contacting Compound II with an acid under aqueous conditions, such that two moles of compound IV are formed having substantially the same optical rotation as the IV initially used in this process. When Z or Z' are not H in II, they are lost during the production of IV.

In Step 6, water miscible solvents can also be present. A preferred molar ratio of Compound II:acid is about 1,000:1 to about 1:1,000; more preferred is about 1:2 to about 1:100. Reaction temperature is preferably about $20°$ to $300°$ C.; preferred is about $50°$ to $200°$ C.; and most preferred is about $100°$ C. Acids are preferably strong acids such as HCl, $H_2SO_4$, HBr, p-toluene sulfonic acid (TsOH), and the like.

More preferred conditions for step 6 include refluxing a solution or suspension of Compound II in aqueous hydrochloric acid.

Alternately, Compound II can be treated with acid in a solvent containing a straight or branched chain alkyl or aryl alcohol to form VIII in high optical purity (i.e., at least about 70%, preferably greater than about 90%).

It is to be understood that certain compounds described herein can exist in salt form. For example, compounds containing an amino moiety, typically readily form acid addition salts such as a hydrochloride, trifluoroacetate, and the like. The salts of such compounds are contemplated to be within the scope of the invention If a salt form of a compound is present, it may be desirable to optionally convert the salt by simple techniques well known in the art to the free base or salt free form of the compound.

All of the process steps described herein are preferably carried out under an inert atmosphere, e.g., under nitrogen or argon. In some cases, the presence of ambient atmosphere is not detrimental.

Preferred processes of the present invention can be represented in the schemes that follow. Rexyn ™ is a tradename for a quaternary ammonium hydroxide anionic exchange resin. The compound numbers can be cross-referenced to the examples.

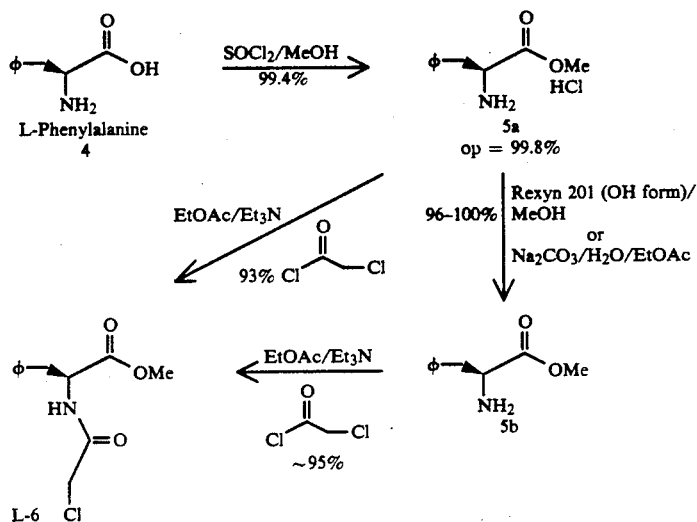

Method A

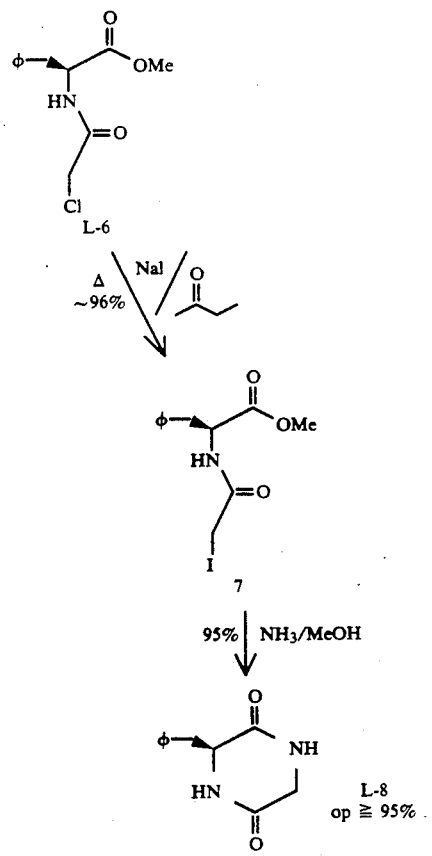

Method B

-continued
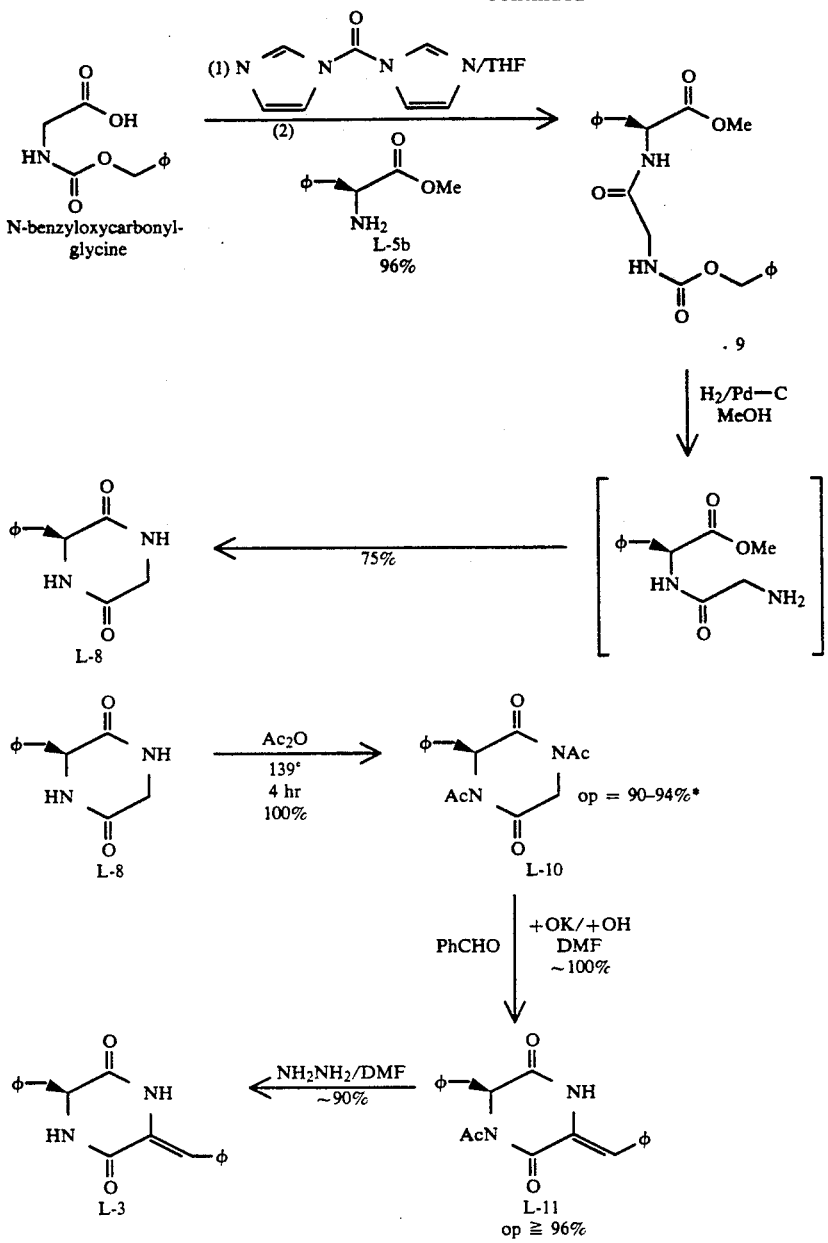
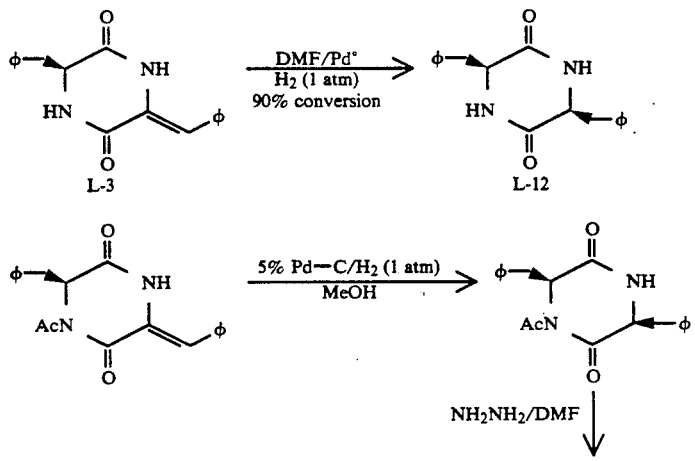
*Optically pure 10 is obtained in 80–88% yield upon crystallization from ethyl acetate-heptane.

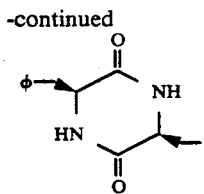

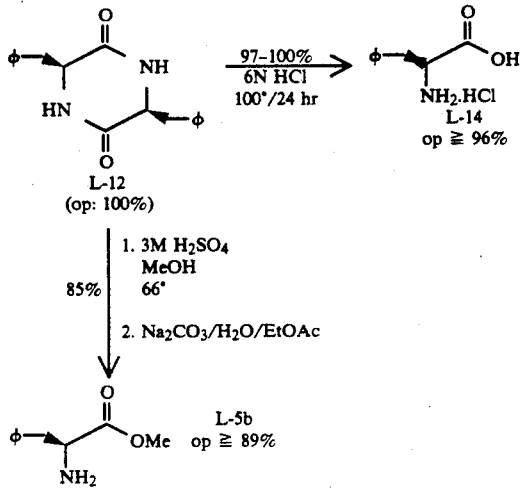

The present invention is illustrated by the following examples; however, such examples should not be interpreted as a limitation upon the scope of the present invention.

EXAMPLES

Example 1

General Procedures

Melting points were determined using a Thomas Hoover capillary melting point apparatus and are uncorrected. Infrared (IR) spectra were recorded on a Perkin-Elmer Model 137 or a Nicolet Model 5DX spectrophotometer and are reported in wave numbers ($cm^{-1}$). All mass spectra (MS) were obtained using a VG Analytical Ltd. Model ZAB-1F Mass Spectrometer in EI (electron impact) and FD (field desorption) modes. GCMS were obtained using a Finnigan 4023 GCMS equipped with a 30 m DB5 capillary column (J & W Scientific) using helium carrier gas. Elemental analyses were performed by Eastman Chemical Division's Physical and Analytical Chemistry Research Division using combustion analysis. Optical rotations were measured using an Autopol III polarimeter manufactured by Rudolph Research.

Unless otherwise specified, all $^1$H NMR spectra were obtained on a JEOL GX-400 NMR instrument operating at 400 MHz. This instrument is capable of a routine resolution of 0.6 Hz.

Chemical shifts are expressed in parts per million relative to internal tetramethylsilane.

High pressure liquid chromatography (HPLC) was accomplished using a Varian 5060 liquid chromatograph equipped with a Zorbax ODS 4.6 mm×25 cm column. Compounds were detected using a Perkin-Elmer LC-75 UV detector at 254 nm. All injections were a 10 mL volume.

Gas chromatography (gc) was accomplished using a Hewlett Packard 5880A instrument in capillary mode using a flame ionization detector unless otherwise specified. Hydrogen was used as a carrier gas at a flow rate of approximately 40 cm/sec. Unless otherwise specified, a 30 m DB5 column (J & W Scientific) was used for GC analyses.

All reactions were carried out under an inert atmosphere of nitrogen or argon unless otherwise specified. Anhydrous tetrahydrofuran (THF) was prepared by distillation from metallic sodium and benzophenone immediately prior to use.

All dimethylformamide (DMF) was distilled using a 1.5×48 in. Podbielniak Helipak column (90 theoretical plates) and only the constant boiling fraction (bp 45° C., 10 mm Hg) was collected. This distilled DMF was stored in the dark under a nitrogen atmosphere and over 4 A sieves. If used within one year, material prepared and stored in this fashion was found to contain less than 35 parts per million of water (Karl Fischer titration) and less than 10 parts per million of dimethyl amine as determined by cation analysis on a Dionex Model 16 ion chromatograph. The sensitivity of this ion chromatography method for dimethyl amine detection was found to be approximately 5 parts per million.

Example 2

L-Phenylalanine Methyl Ester Hydrochloride

Thionyl chloride (14 mL, 0.19 mol) was slowly added to a vigorously stirred —5° C. suspension of L-phenylalanine (26.28 g, 0.159 mol) in methanol (250 mL). After the addition of thionyl chloride was complete, the resulting homogeneous solution was allowed to warm to room temperature and was left stirring overnight. The reaction solvent was removed invacuo to produce a white solid. This solid was redissolved in methanol (100 mL) and the resulting solution was reconcentrated in vacuo to produce the product L-phenylalanine methyl ester hydrochloride (mp 158°-159° C., 34.10 g, 0.158 mol, 99.4%). A sample of this material was converted to the N-trifluoroacetylisopropyl ester using standard procedures. The resulting ester was found to contain 0.088% of the D-isomer by gc analysis on a Chirasil-Val ™ chiral gc column (obtained from Applied Science). The $^1$H NMR of this synthetic material was identical with that of a commercial sample.

$^1$H NMR (DMSO-d6): δ=8.62 (bs, 2.1H), 7.35–7.22 (m, 5H), 4.27 (apparent t, J~6.1, 6.7, 1H), 3.67 (s, 3H), 3.18 (dd, J=6.1, 14.0, 1H), 3.10 (dd, J=7.3, 14.0, 1H)

Optical Rotation: [α]$_D^{25}$= +37.4° (c=1.95, EtOH)

Analysis: Calc. for C10H13NO2HCl: C, 55.69; H, 6.54; N, 6.49; Cl, 16.44.

Found: C, 55.70; H, 6.56; N, 6.43; Cl, 16.29

Example 3

N-α-Chloroacetyl-L-phenylalanine Methyl Ester

Chloroacetyl chloride (19 mL, 0.24 mol) was added over a period of approximately 5 minutes to a vigorously stirred, 0° C. suspension of distilled triethylamine (70 mL, 0.50 mol) and L-phenylalanine methyl ester hydrochloride (49.95 g, 0.232 mol) in ethyl acetate (400 mL). After a period of 30 minutes at 0°–10° C., the reaction mixture was filtered to remove triethylamine hydrochloride. The resulting solution was extracted with 1N HCl (2×250 mL), water (250 mL), half-saturated aqueous sodium carbonate (2×250 mL), and brine (2×200 mL). The organic phase was filtered through magnesium sulfate and sodium sulfate and concentrated in vacuo to provide the product, 6, as light brown crystals (mp 72.5°–75° C., 55.26 g, 0.216 mol, 93.4%). This material was found to be of suitable purity (>95% by NMR) for use in subsequent reactions (vide infra). An analytical sample of 6 (mp 76°–77° C.) could be prepared upon crystallization from methanol-water (2/1).

$^1$H NMR (CDCl3): δ=7.33–7.10 (m, 5H), 6.97 (bd, J~6.1, 1H), 4.87 (m, 1H), 4.04 (d, J=15.3, 1H), 4.00 (d, J=15.3, 1H), 3.74 (s, 3H), 3.17 (dd, J=6.1, 14.0, 1H), 3.13 (dd, J=6.1, 14.0, 1H)

FDMS: M+ =255

IR (KBr): ν=3360, 3175–2860, 1740, 1660, 1550

Example 4

N-α-Iodoacetyl-L-phenylalanine Methyl Ester

N-α-Chloroacetyl-L-phenylalanine methyl ester (6, 10.61 g, 0.0415 mol) was added to a solution of sodium iodide (10.34 g, 0.069 mols) in 2-butanone (100 mL). The resulting solution was refluxed for 2 hours and 45 minutes. The reaction mixture was filtered to remove precipitated sodium chloride and the 2-butanone was removed in vacuo. The product was dissolved in ethyl acetate and extracted with water and brine. The organic phase was dried by filtration through magnesium sulfate and sodium sulfate and concentrated in vacuo to provide 7 as a yellow-brown crystalline solid (14.04 g, ~0.040 mol, ~98%). This material was not purified further and was found to be of suitable purity for use in the preparation of cyclo-glycyl-L-phenylalanine, 8 (vide infra).

$^1$H NMR (CDCl3): δ=7.33–7.12 (m, 5H), 6.48 (bd, J=7.3, 1H), 4.85 (m, 1H), 3.75 (s, 3H), 3.69 (d, J=11.6, 1H) 3.65 (d, J=11.6, 1H), 3.17 (dd, J=6.1, 14.0 1H), 3.11 (dd, J=6.1, 14.0, 1H)

FDMS: M+ =347

IR (KBr): ν=3330, 3175–2860, 1754, 1667, 1544

Exact mass: Calc. for C12H14NO3I: 347.0017

Found: 347.0030.

Example 5

N-Benzyloxycarbonyl-glycyl-L-phenylalanine Methyl Ester

Solid carbonyldiimidazole (79.10 g, 0.488 mol) was added to a room temperature solution of N-benzyloxycarbonyl-glycine (117.11 g, 0.560 mol) in anhydrous tetrahydrofuran (THF, 600 mL). The resulting solution was stirred for 45 minutes until $CO_2$ evolution had ceased. A solution of L-phenylalanine methyl ester (79.65 g, 0.444 mol) in anhydrous THF (~200 mL) was then added. The reaction temperature was maintained below 40° C. by application of a water bath to the exterior of the reaction vessel. After two hours, a small portion of water (1.5 mL, ~0.08 mol) was added to the reaction mixture to hydrolyze any remaining acylimidazolides and the resulting solution was left to stir overnight. The reaction mixture was concentrated in vacuo and the residual oil was dissolved in ethyl acetate (~1 L). This ethyl acetate solution was extracted with 1 N HCl (2×300 mL—the first aqueous extract was acidified a pH of 1 by addition of 6 N HCl), water (300 mL), saturated aqueous sodium carbonate (300 mL), half-saturated aqueous sodium carbonate (250 mL), and brine (250 mL). The organic phase was dried by filtration through magnesium sulfate and sodium sulfate and concentrated in vacuo to constant weight. Field desorption mass spectrometry (FDMS) of the resulting oil (160.88 g, ~0.434 mol, 98%) indicated the presence of a single component (M+ =370). This material was not further purified, but was instead converted directly into cyclo-glycyl-L-phenylalanine (8) by catalytic hydrogenation (vide infra).

$^1$H NMR (CDCl3): δ7.34–7.06 (m, 10H), 6.49 (bd, J=6.7, 1H), 5.43 (bs, 1H), 5.11 (s, 2H), 4.87 (dd, J=6.1, 6.1, 1H), 3.84 (m, 2H), 3.71 (s, 3H), 3.12 (dd, J=6.1, 14.0, 1H), 3.07 (dd, J=6.1, 14.0, 1H)

FDMS: M+ =370

IR (film): ν=3330, 3175–2860, 1740, 1680, 1540

Example 6

Cyclo-glycyl-L-phenylalanine, Method A

N-α-Iodoacetyl-L-phenylalanine methyl ester (7, 2.85 g, 0.0082 mol) was added to a freshly prepared saturated solution of NH3 in methanol (145 mL) at 18° C. The resulting homogeneous solution was allowed to stand overnight at room temperature. The white precipitate of 8 (0.94 g, 0.0046 mol, 56%) which had formed overnight was collected by filtration. This material was shown to be of high purity by $^1$H NMR(identical with material prepared by Method B) and optical rotation [α]$_D^{25}$= +125° C., c=0.228, CF3COOH). The filtrate was concentrated in vacuo to provide an additional sample of 8 (1.87 g) which was contaminated with inorganic salts. External standard HPLC analysis indicated that this second material had a purity of 35%. Thus, the combined yield of 8 in this reaction was 95%.

Example 7

Cyclo-glycyl-L-phenylalanine (8), Method B

A solution of N-benzyloxycarbonyl-glycyl-L-phenylalanine methyl ester (9, 160.83 g, 0.434 mol) in methanol (500 mL) was added to a vigorously stirred suspension of 5% palladium on carbon (11.4 g) in methanol (1 L). Argon was bubbled through the reaction mixture for 15 minutes. Hydrogen was then introduced into the reaction vessel at a rate such that a slow flow of hydrogen gas (1 atm) was maintained through the vessel. Before completion of the reaction, it was necessary to apply a cooling bath to prevent loss of methanol due to the mildly exothermic nature of the reaction. After a period of three hours (hydrogen uptake had ceased after two hours), the reaction vessel was purged with argon and the reaction mixture was filtered through celite. Additional methanol was added to the filtrate to bring the final volume to 3.5 litres. This solution was set aside at room temperature for a period of one week. Filtration of the resulting precipitate provided the product 8 (mp 267°-269° C., dec; [ ]$D^{25}$ = +133.8°, c=0.204, CF$_3$COOH) as a white solid (66.76 g, 0.327 mole, 75%).

This second filtrate was set aside and after a period of 2-3 weeks all precipitation appeared to cease. Filtration of the precipitate provided an additional crop of 8 (4.57 g, 5.1%).

An analytical sample of 8 (mp 269.5°-270.5° C., dec. was prepared by recrystallization of the first filtrate from hot methanol ([$\alpha$]$_D^{25}$ = +133.2°, c=0.202, CF$_3$COOH).

$^1$H NMR (DMSO-d$_6$): $\delta$=8.16 (bs, 1H), 7.89 (bs, 1H), 7.30-7.16 (m, 5H), 4.07 (m, 1H), 3.34 (d, J=17.7, 1H), 3.09 (dd, J=4.3, 13.4, 1H), 2.88 (dd, J=4.9, 13.4, 1H), 2.76 (d, J=17.7, 1H)

FDMS: M+ =204

IR (KBr): $\nu$=3330-2860, 1680, 1470

Analysis: Calc. for C$_{11}$H$_{12}$N$_2$O$_2$: C, 64.69; H, 5.92; N, 13.72

Found: C, 64.62; H, 5.77; N, 13.51

Example 8

N,N'-Diacetyl-cyclo-glycyl-L-phenylalanine (10)

A stirred suspension of cyclo-glycyl-L-phenylalanine (8, 41.03 g, 0.201 mol) in acetic anhydride (390 mL) was heated to reflux. In approximately 20 minutes, the reaction mixture became homogeneous. After a period of 3 hours and 40 minutes at reflux, the now pale yellow reaction mixture was cooled and the solvent was removed in vacuo. The viscous oil crystallized when seeded with a previously prepared sample of 10. Except for traces of what appeared to be acetic anhydride and acetic acid, this crude crystalline product (62.3 g, 107%) was shown to be a single component by $^1$H NMR. An analytical sample of 10 (mp 102°-103° C., 45.81g, 0.159 mol, 80%) was prepared upon crystallization of this material (61.67 g) from hot ethyl acetate (100 ml) and heptane (1.1 L). The residual liquid from this crystallization was concentrated in vacuo and the resulting pale yellow crystals were dried under high vacuum (0.5 mm, 35° C., 18 hours) to constant weight (11.49 g, 0.40 mol, 20%). Both of these samples obtained from this crystallization were shown to be identical by $^1$H NMR.

The optical purity of the analytical sample ([$\alpha$]D$^{23}$~ +61.56°, c=0.307, EtOH; [$\alpha$]D$^{25}$= +79.6, c=0.353, EtOAc) was found to be greater than 98% when analyzed by 400 MHz NMR (CDCl$_3$) in the presence of the chiral shift reagent (−)2,2,2-trifluoro-1-(9-anthryl)-ethanol. However, when analyzed by this same method, the material isolated from the mother liquors was found to contain between 15 and 25% of the D isomer.

In a repetition of this experiment (10 g scale), an 86% yield of optically pure recrystallized product was obtained.

$^1$H NMR (CDCl$_3$): $\delta$=7.35-7.05 (m, 5H), 5.45 (apparent t, J~4.9, 1H), 4.49 (d, J=18.9, 1H), 3.35 (dd, J=4.3, 14.0, 1H), 3.21 (dd, J=5.5, 14.0 1H), 2.59 (s, 3H), 2.56 (s, 3H), 2.46 (d, J=18.9, 1H)

FDMS: M+ =288

IR (KBr): $\nu$=3175-2860, 1724

Analysis: Calc. for C$_{15}$H$_{16}$N$_2$O$_4$: C, 62.49; H, 5.59; N, 9.72

Found: C, 62.17, H, 5.51; N, 9.49

Example 9

(S)-1-Acetyl-3-benzylidene-6-benzyl-2,5-piperazinedione

A freshly prepared solution of potassium t-butoxide in t-butyl alcohol (~0.88 M, 16.9 mL, 0.015 mol) was slowly added over a 45-minute period to a 5°-10° C. solution of the recrystallized diketopiperazine 10 (4.27 g, 0.0148 mol) and benzaldehyde (3.0 mL, 0.030 mol) in distilled anhydrous dimethylformamide (15 mL). After the addition of base was completed, a very thick suspension of salts had resulted. This suspension was stirred at 10° C. for 30 minutes and then for 2.5 hours at room temperature. The solvent was removed in vacuo and the reaction mixture was dissolved in ethyl acetate (100 mL). This solution was filtered to remove a small amount of a white precipitate and was then extracted with water (100 mL). The organic phase was dried over magnesium sulfate and concentrated in vacuo to provide the product 11 (5.21 g, 105%) as a viscous oil which was shown to contain traces of ethyl acetate (~6 mole %) and benzaldehyde (~20 mole %) by $^1$H NMR. This material was not purified further, but was instead converted to the insoluble desacetyl diketopiperazine 3 (vide infra). $^1$H NMR analysis using the chiral shift reagent (−)-2,2,2,-trifluoro-1-(9-anthryl)ethanol in CDCl$_3$ indicated that there was 1% or less of the D-isomer in 11 when prepared by the above method.

$^1$H NMR (CDCl$_3$); $\alpha$=7.75 (bs, 1H), 7.41-7.09 (m, 10H), 6.61 (s, 1H), 5.37 (apparent t, J~4.5, 1H), 3.30 (dd, J=4.3, 14.0, 1H), 3.25 (dd, J=5.5, 14.0, 1H), 2.62 (s, 3H)

FDMS: M+ =334

Exact mass: Calc. for C$_{20}$H$_{18}$N$_2$O$_3$:334.1313

Found: 334.1325

Optical Rotation: [$\alpha$]D$^{25}$= −456° (c=0.89, EtOH);

Example 10

(S)-3-Benzylidene-6-benzyl-2,5-piperazinedione

Hydrazine hydrate (1 mL, ~0.021 mol) was added to a vigorously stirred solution of diketopiperazine 11 (4.67 g, ~0.014 mol) in DMF (30 mL). There occurred an almost instantaneous precipitation of the product as a white solid. The reaction mixture was concentrated in vacuo and triturated with cold water (3×7 mL). The product (3.74 g, ~0.013 mol, ~92%) was dried to constant weight in vacuo and was shown to be of high purity by $^1$H NMR (with the exception of ~20 mole % of DMF). An analytical sample of 3 (mp 288°-289° C., was prepared by recrystallization of the precipitate from hot acetic acid-methanol (⅓, v/v).

$^1$NMR (DMSO-d$_6$): $\delta$=9.71 (bs, 1H), 8.45 (bs, 1H), 7.35-7.12 (m, 10H), 6.33 (s, 1H), 4.34 (bs, 1H), 3.15 (dd, J=4.3, 13.4, 1H), 2.97 (dd, J=4.9, 13.4, 1H)

FDMS: M+ =292

IR (KBr): $\nu$=3204, 3062, 1671, 1632, 1499, 1454, 1435, 1402, 1350, 1313, 1206, 1194, 1094, 924, 910, 874, 860, 822, 738, 638

Analysis: Calc. for $C_{18}H_{16}N_2O_2$: C, 73.96; H, 5.52; N, 9.58

Found: C, 73.79; H, 5.40; N, 9.42

UV (95%) ethanol): $\lambda max = 295$ nm; log $\epsilon = 4.295$

Optical Rotation: $[\alpha]D^{25} = -542°$ (c=0.0306, HOAc);

Example 11

Cyclo-L-phenylalanyl-L-phenylalanine

Palladium black (0.1 g) was added to a vigorously stirred suspension (under argon) of the dehydrodiketopiprazine 3 (0.73 g, 0.0025 mol) in DMF (90 mL). Hydrogen (1 atm) was then introduced into the reaction vessel. After a period of three days, gas chromatographic analysis (gc) of the reaction mixture indicated incomplete reaction. A second portion of palladium black (0.2 g) was added to the reaction. The reaction suspension was stirred for an additional four days under a hydrogen atmosphere. The reaction product was dissolved in 250 mL of hot DMF and filtered to remove catalyst. Concentration in vacuo provided 12 as a white solid (0.63 g, 0.0022 mol, 85%). HPLC analysis of this sample indicated that the ratio of cis- to trans-isomer in this sample was 99/1. Except for the presence of approximately 3% of the dehydrodiketo-piperazine 3, the 400 MHz 1H NMR of this material was identical with a sample of 11 which had been prepared previously by an independent method of synthesis. A sample of the reduction product 12 (prepared as described above) was hydrolyzed in refluxing 6N HCl (20 hr) and converted into the N-trifluoroacetyl-isopropyl ester of phenylalanine by standard procedures. The ratio of D to L isomer as determined by gc analysis on a Chirasil-Val TM capillary gc column was found to be 4.2/95.8.

Example 12

DL-1-Acetyl-3,6-cis-dibenzyl-2,5-piperazine-dione (DL-13)

Hydrogen (1 atm) was introduced into a reaction vessel containing 5% palladium on carbon (0.1 g), the DL-N-acetyl-diketopiperazine 11 (1.07 g, 0.0032 mol) and methanol (50 mL). After a period of 22 hours, the reaction was filtered through a Milex-HV 0.45 μm filter unit and concentrated in vacuo to provide the product DL-13 as a viscous oil (0.92 g, 0.0027 mol, 85%). In addition to indicating a high level of purity, 1H NMR indicated the presence of the cis-isomer as the major component (the ratio of cis to trans-isomer was estimated to be approximately 12 to 1 or greater). Further evidence for the presence of a major cis- and a minor trans-isomer was obtained from the gc/ms which indicated the presence of two isomeric components (MWT 336) in a ratio of 13/1.

1H NMR (CDCl$_3$-D$_2$O): $\delta = 7.42$–7.12 (m, 10H), 5.19 (apparent t, J=3.7, 4.9 1H) 4.02 (dd, J=3.0, 11.6, 1H), 3.34 (dd, J=3.7, 14.0, 1H), 3.23 (dd, J=4.9, 14.0, 1H), 2.87 (dd, J=3.0, 13.5, 1H), 2.65 (s, 3H), 0.80 (dd, J=11.6, 13.5, 1H)

Example 13

Preparation of L-Phenylalanine Methyl Ester (5b) From Cyclo-L-phenylalanyl-L-phenylalanine (12)

Cyclo-L-phenylalanyl-L-phenylalanine (12, 1.73 g, 0.0059 mol) was added to a 3M solution of concentrated sulfuric acid in methanol (50 mL). The solution was brought to reflux (66° C.) and the initially heterogeneous solution became homogeneous in several hours (intermediate formation of the sulfate salt of L-phenylalanyl-L-phenylalanine methyl ester). The progress of the reaction was periodically monitored by gc (after addition to saturated sodium carbonate and extraction with ethyl acetate). Approximately 6 days at reflux was required to convert 50% of the reaction mixture to L-phenylalanine methyl ester. After refluxing for a period of 17 days, the reaction mixture was cooled to room temperature and added to an ice-cold mixture of saturated aqueous sodium carbonate (250 mL), 2N sodium hydroxide (50 mL), and ethyl acetate (250 mL). The organic phase was removed and the aqueous phase (pH 11) was repeatedly extracted with ethyl acetate (3×250 mL). The combined organic phases were dried by filtration through sodium sulfate and concentrated in vacuo to provide ester 5b (1.79 g, 0.010 mol, 85%) as a pale yellow oil. The identity and chemical purity of the L-phenylalanine methyl ester prepared by this method was established by comparison of the 1H NMR for this material with the 1H NMR for a sample of ester 5b obtained by an independent method. The D-isomer content for ester 5b when prepared by the above method was determined to be 5.5% by gc analysis (after derivatization to the N-trifluoroacetyl isopropyl ester) on a Chirasil-Val TM capillary column.

Example 14

Preparation of L-Phenylalanine Hydrochloride (14) From Cyclo-L-phenylalanyl-L-phenylalanine Cyclo-L-phenylalanyl-L-phenylalanine (12, 1.0818 g, 0.0036 mol) was added to a solution of 6N HCl (40 mL). The reaction mixture was brought to reflux and over a period of 8 hours the initially heterogeneous solution turned homogeneous. After a total of 24 hours at reflux, the reaction mixture was concentrated in vacuo. An unsuccessful attempt was made to convert the hydrochloride product 14 to L-phenylalanine by redissolving the crude product in distilled water (6×30 mL) followed by removal of the solvent under high vacuum (0.5 mm, 45° C.). The resulting material (1.4337 g, ~0.0036 mol, ~100%) was dried to constant weight and was verified to be phenylalanine hydrochloride by elemental analysis. This material was found to contain 1.9% of the D-isomer by analysis (after derivatization to the N-trifluoroacetyl isopropyl ester) on a Chirasil-Val capillary gc column.

1H NMR (D$_2$O): $\delta = 7.44$–7 32 (m, 5H), 3.99 (dd, J=5.5, 7.9, 1H), 3.29 (dd, J=5.5, 14.6, 1H), 3.13 (dd, J=7.9, 14.6, 1H)

FDMS: 166 (—Cl)

Analysis: Calc. for $C_9H_{12}NO_2Cl$: C, 53.61; H, 5.60; N, 6.95; Cl, 17.58

Found C, 53.29; H, 5.96; N, 6.85; Cl, 16.9

We claim:

1. A compound of the formula

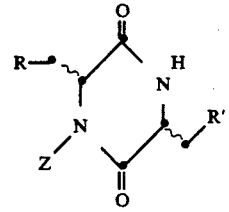

wherein R is alkyl, hydroxy, $C_1$ to $C_{10}$ alkoxy $C_1$ to $C_{10}$ carboxyalkyl, $C_1$ to $C_{10}$ acyloxy, phenyl optionally substituted with one to four moieties chosen from the group consisting of halogen, hydroxy, protected hydroxy, cyano, nitro, $C_1$ to $C_4$ alkyl, $C_1$ to $C_4$ alkoxy, carboxy, carboxymethyl, hydroxymethyl, aminomethyl, trifluoromethyl and n-(methylsulfonylamino) or phenyl($C_1$ to $C_6$)alkyl wherein the alkyl portion is optionally substituted with one or two moieties chosen from the group consisting of halogen, hydroxy, $C_1$ to $C_7$ acyloxy, nitro carboxy, carbamoyl, carbamoyloxy, cyano, N-(methylsulfonylamino), and $C_1$ to $C_4$ alkoxy, and the phenyl portion is optionally substituted with one or two moieties chosen from the group consisting of halogen, hydroxy, nitro, $C_1$ to $C_4$ alkyl, $C_1$ to $C_4$ alkoxy, carboxy, carboxymethyl, hydroxymethyl, aminomethyl, and N-(methylsulfonylamino); R' is the same as R: and Z is a nitrogen-protecting group.

2. The compound of claim 1 wherein Z is acyl or acyloxy and both R and R' are the same and are said phenyl, optionally substituted.

3. The compound of claim 2 wherein Z is acetyl or alpha-halo-acetyl.

4. A compound of the formula

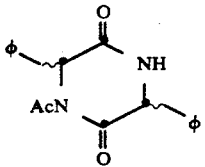

wherein Ac is acetyl.

5. The compound of claim 1 wherein the diastereomeric and optical purity of the compound are at least 90% of the cis derivative, and wherein both asymmetric carbon atoms are substantially of both D or both L configuration.

6. The compound of claim 5 wherein the diastereomeric and optical purity of the compound are at least 95% of the cis derivative 7. The compound of claim 3 wherein R and R' are phenyl.

8. The compound of claim 4 wherein the diastereomeric and optical purity of the compound are at least 90% of the cis derivative, and wherein both asymmetric carbon atoms are substantially of both D or both L configuration.

9. The compound of claim 8 wherein the diastereomeric and optical purity of the compound are at least 95% of the cis derivative.

* * * * *